United States Patent
Park et al.

(10) Patent No.: US 11,185,607 B2
(45) Date of Patent: Nov. 30, 2021

(54) PREPARATION METHOD OF CALCIUM PEROXIDE-MEDIATED IN SITU CROSSLINKABLE HYDROGEL AS A SUSTAINED OXYGEN-GENERATING MATRIX, AND BIOMEDICAL USE THEREOF

(71) Applicants: INCHEON UNIVERSITY INDUSTRY ACADEMIC COOPERATION FOUNDATION, Incheon (KR); AJOU UNIVERSITY INDUSTSRY-ACADEMIC COOPERATION FOUNDATION, Suwon-si (KR)

(72) Inventors: Kyung Min Park, Anyang-si (KR); Ki Dong Park, Seoul (KR); Su Jin Park, Incheon (KR)

(73) Assignees: INCHEON UNIVERSITY INDUSTRY ACADEMIC COOPERATION FOUNDATION, Incheon (KR); AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 466 days.

(21) Appl. No.: 16/322,491

(22) PCT Filed: Aug. 3, 2017

(86) PCT No.: PCT/KR2017/008386
§ 371 (c)(1),
(2) Date: Feb. 1, 2019

(87) PCT Pub. No.: WO2018/026204
PCT Pub. Date: Feb. 8, 2018

(65) Prior Publication Data
US 2021/0330858 A1    Oct. 28, 2021

(30) Foreign Application Priority Data

Aug. 4, 2016    (KR) ..................... 10-2016-0099495

(51) Int. Cl.
*A61K 33/08*    (2006.01)
*A61L 27/52*    (2006.01)
(Continued)

(52) U.S. Cl.
CPC ............ *A61L 24/104* (2013.01); *A61K 47/42* (2013.01); *A61L 24/0031* (2013.01);
(Continued)

(58) Field of Classification Search
CPC .... A61L 27/52; A61L 24/104; A61L 2300/11; A61K 47/42; A61K 33/08; C08J 3/24
See application file for complete search history.

(56) References Cited

U.S. PATENT DOCUMENTS

2012/0156164 A1    6/2012    Park et al.

FOREIGN PATENT DOCUMENTS

| KR | 10-2011-0025530 A | 3/2011 |
| KR | 10-2011-0056630 A | 5/2011 |
| KR | 10-1573571 B1 | 12/2015 |

OTHER PUBLICATIONS

Alemdar et al. (Biomater. Sci. Eng. 2017;3:1964-1971) (Year: 2017).*

(Continued)

*Primary Examiner* — Ernst V Arnold
(74) *Attorney, Agent, or Firm* — Revolution IP, PLLC

(57) ABSTRACT

A preparation method of calcium peroxide-mediated in situ crosslinkable hydrogel as a sustained oxygen-generating matrix, includes: a) reacting a natural or a synthetic polymer with Traut's reagent (TR) in a solvent, and synthesizing a polymer derivative having thiol group in backbone of the
(Continued)

polymer derivative; and b) mixing and reacting a solution of the polymer derivative having thiol group with calcium peroxide ($CaO_2$), and thereby forming a hydrogel, wherein in the step b), disulfide bonds (—S—S) are induced between backbones of the polymer derivative having thiol group attached by decomposition of calcium peroxide ($CaO_2$), and thereby in situ crosslinking is formed.

18 Claims, 9 Drawing Sheets

(51) Int. Cl.
| | |
|---|---|
| A61K 47/42 | (2017.01) |
| A61L 24/10 | (2006.01) |
| A61L 24/00 | (2006.01) |
| A61L 27/22 | (2006.01) |
| C08L 89/06 | (2006.01) |
| C08J 3/24 | (2006.01) |
| C08J 3/075 | (2006.01) |

(52) U.S. Cl.
CPC ............ *A61L 27/222* (2013.01); *A61L 27/52* (2013.01); *C08J 3/075* (2013.01); *C08J 3/24* (2013.01); *C08L 89/06* (2013.01); *A61L 2300/802* (2013.01); *A61L 2400/06* (2013.01); *C08L 2201/52* (2013.01); *C08L 2203/02* (2013.01); *C08L 2312/00* (2013.01)

(56) References Cited

OTHER PUBLICATIONS

Gholipourmalekabadi et al. (Trends in Biotechnology 2016;34(12):1010-1021) (Year: 2016).*
Pedraza et al. (PNAS 2012;109(11):4245-4250) (Year: 2012).*
International Search Report for PCT/KR2017/008386 dated Dec. 15, 2017 from Korean Intellectual Property Office.
Vlierberghe, Sandra Van et al., "Reversible gelatin-based hydrogels: Finetuning of material properties", European Polymer Journal, 24 Feb. 2 (online), vol. 47, pp. 1039-1047.
Camci-Unal, Gulden et al., "Oxygen-releasing biomaterials for tissue engineering", Polymer International, Apr. 3, 2013 (online), vol. 62, pp. 843-848.
Gyarmati, Benjamin et al., "RReversible disulphide formation in polymer networks: A versatile functional group from synthesis to applications", European Polymer Journal, Mar. 25, 2013 (online), vol. 49, pp. 1268-1286.

* cited by examiner

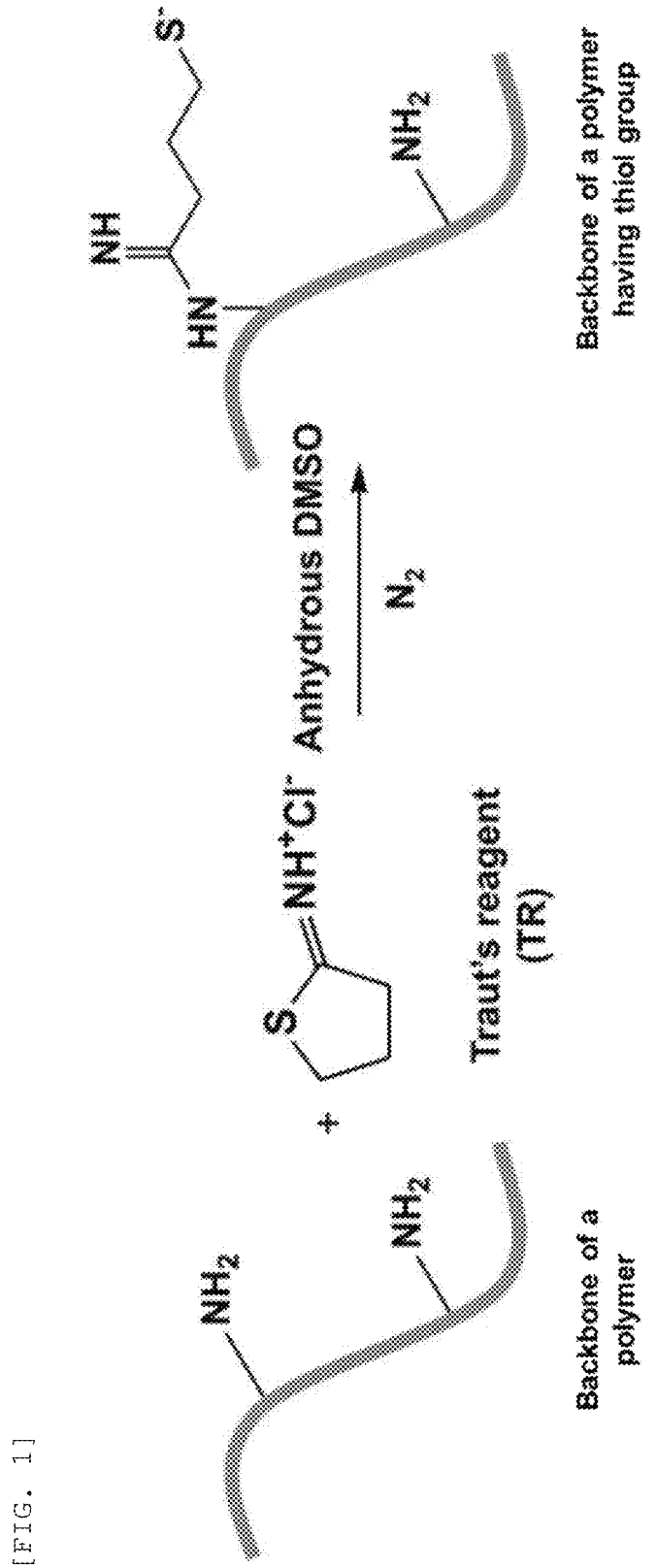
[FIG. 1]

[FIG. 2]
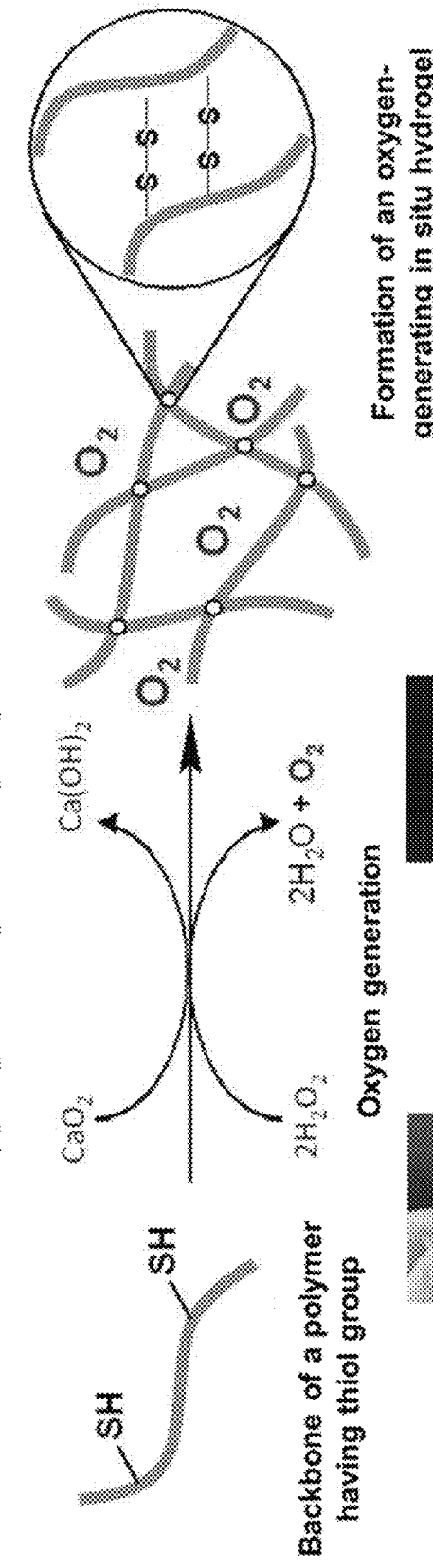

[FIG. 3]
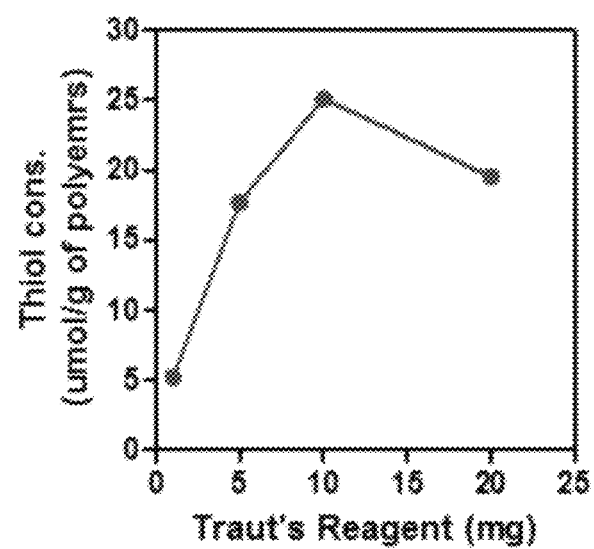

[FIG. 4]
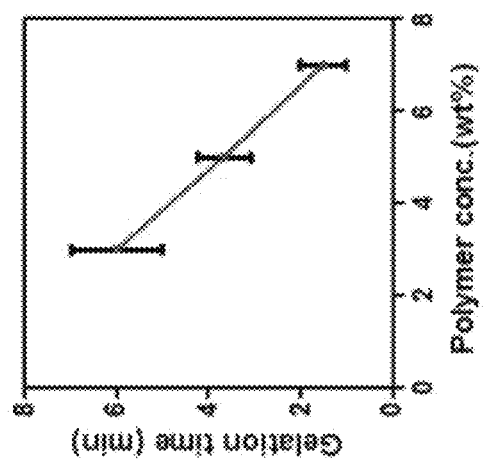
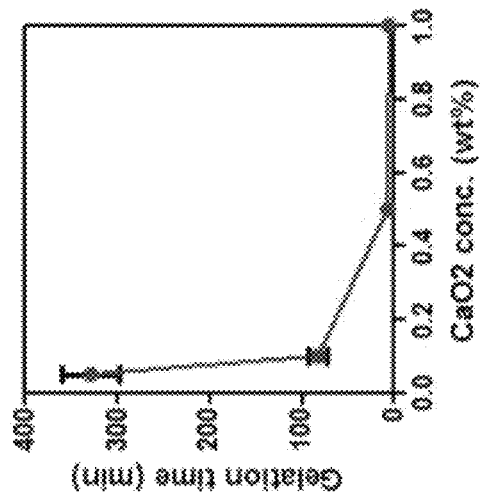
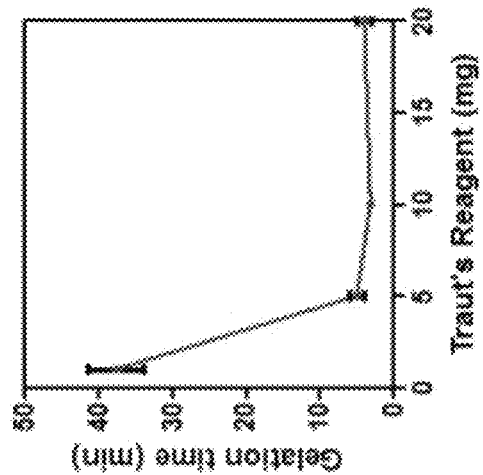

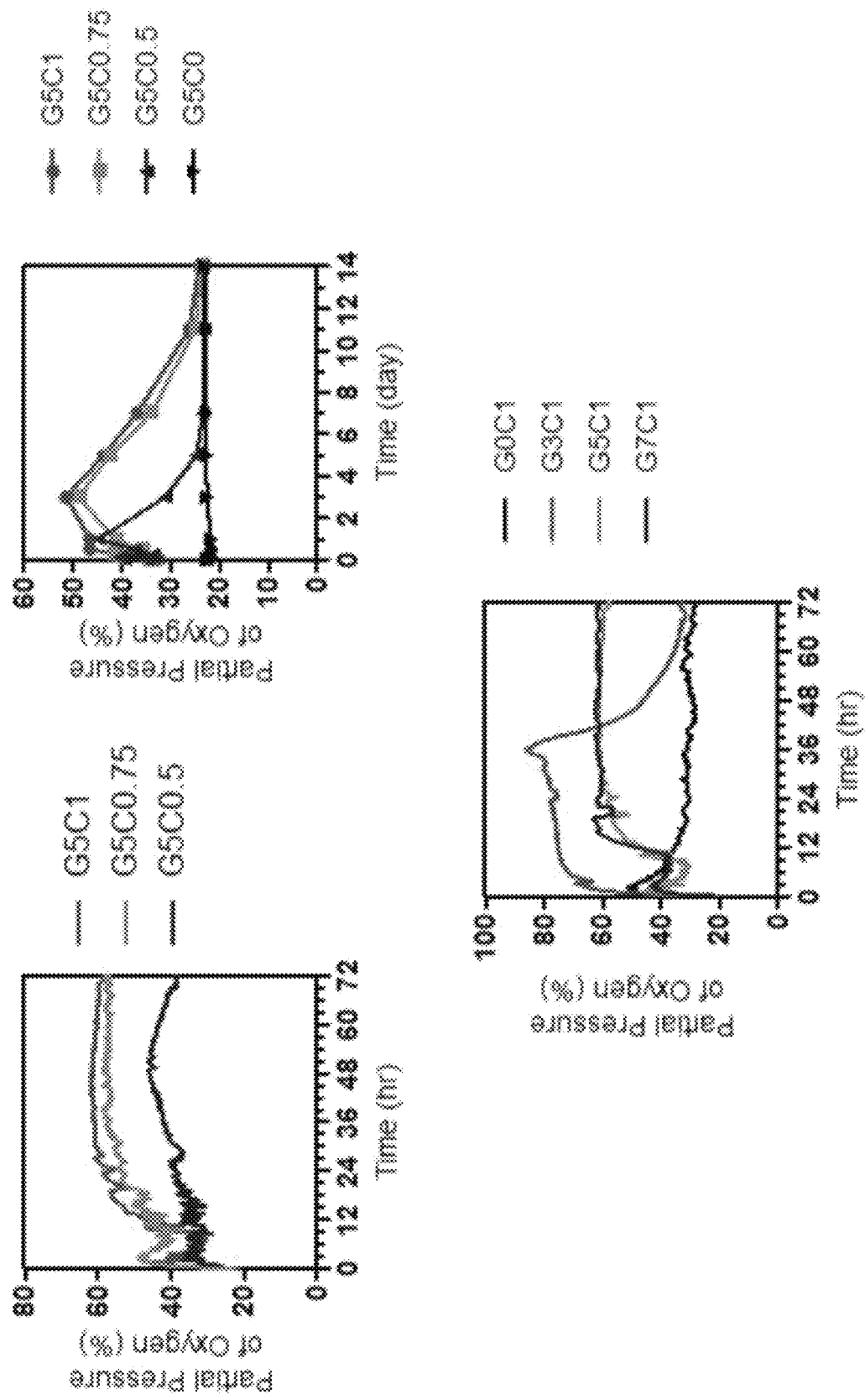
[FIG. 5]

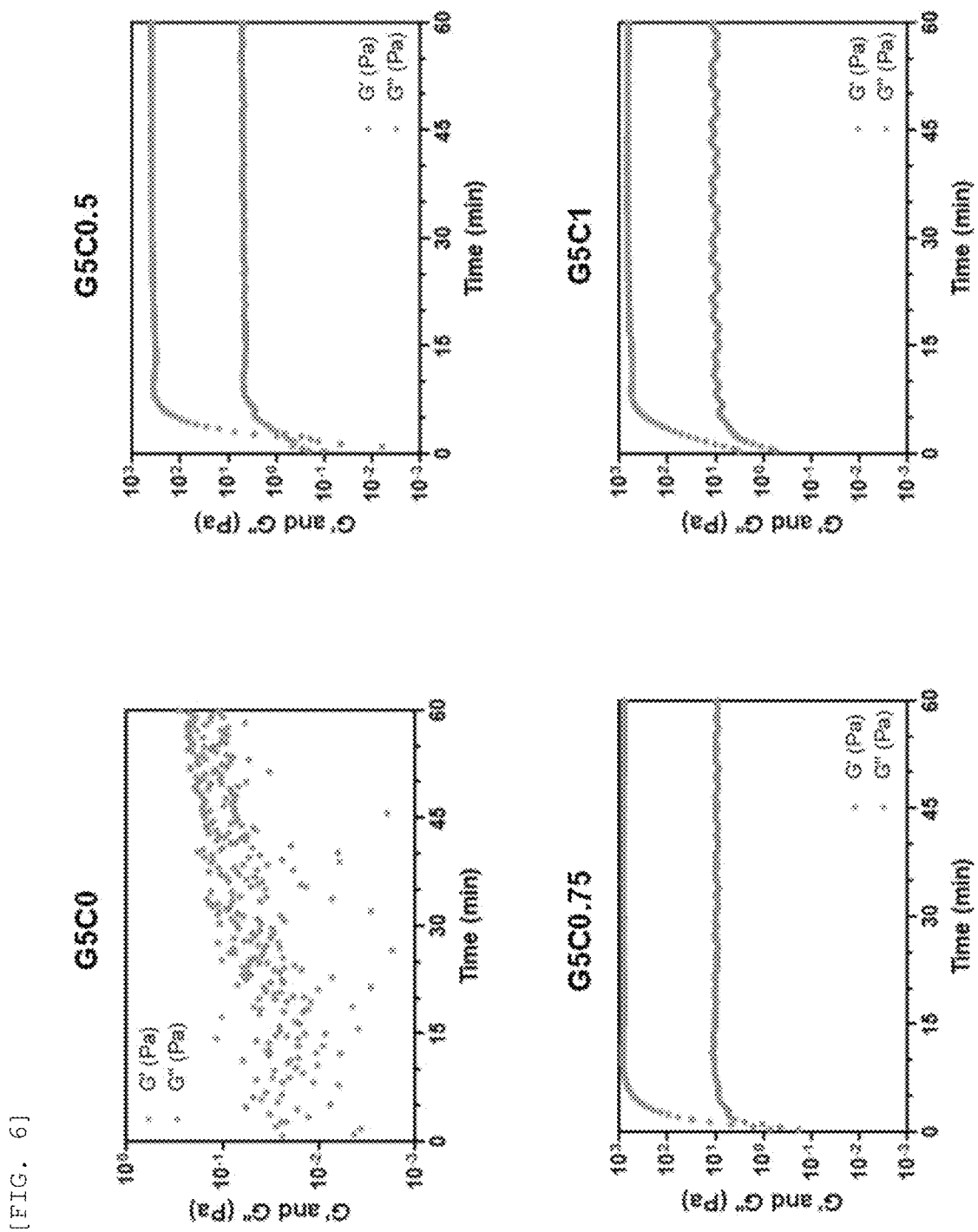
[FIG. 6]

[FIG. 7]
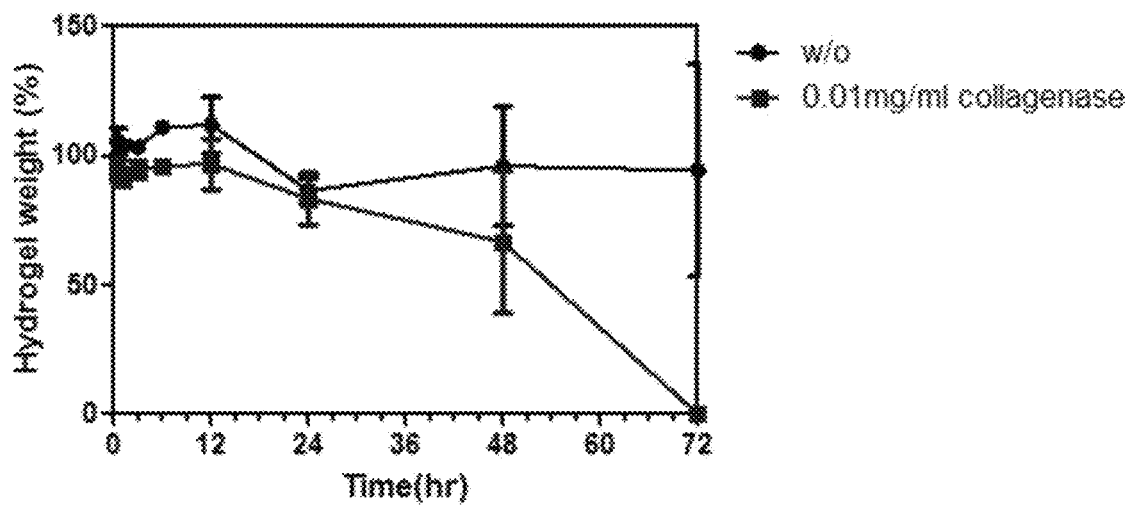

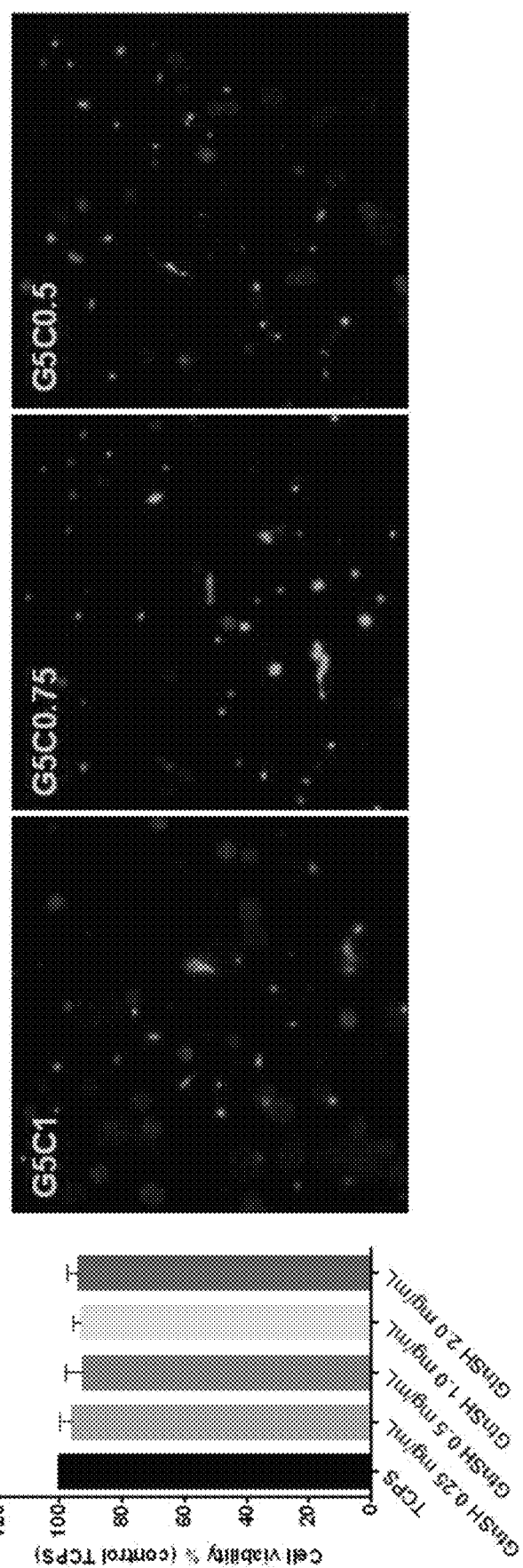
[FIG. 8]

[FIG. 9]
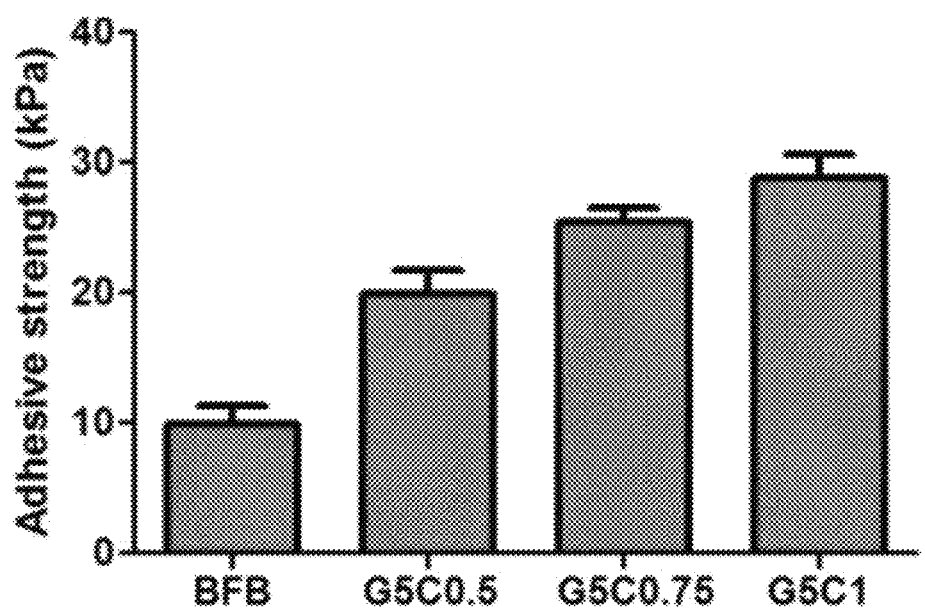

PREPARATION METHOD OF CALCIUM PEROXIDE-MEDIATED IN SITU CROSSLINKABLE HYDROGEL AS A SUSTAINED OXYGEN-GENERATING MATRIX, AND BIOMEDICAL USE THEREOF

ACKNOWLEDGEMENTS

[Supporting National Research and Development Project]
[Project Number] 2015R1C1A1A01054498
[Sponsor] Ministry of Science and ICT
[Specialized Institution] National Research Foundation of Korea (NRF)
[Project Name] Personal Basic Research
[Research Subject] Development of tumor-vascular model using functional polymer hydrogel and hypoxia/reactive oxygen induction culture technology
[Contribution Rate] 1/4
[Research Managing Institution] INU RESEARCH & BUSINESS FOUNDATION
[Research Period] Nov. 1, 2017 through Oct. 31, 2018
[Supporting National Research and Development Project]
[Project Number] 2015R1A2A1A14027221
[Sponsor] Ministry of Science and ICT
[Specialized Institution] National Research Foundation of Korea (NRF)
[Project Name] Personal Basic Research
[Research Subject] Development of bioactive injection hydrogel and human stem cell-based tissue regeneration application technology for vascular disease
[Contribution Rate] 1/4
[Research Managing Institution] AJOU UNIVERSITY INDUSTRY-ACADEMIC COOPERATION FOUNDATION
[Research Period] Sep. 1, 2017 through Aug. 31, 2018
[Supporting National Research and Development Project]
[Project Number] 2015M3A9E2028578
[Sponsor] Ministry of Science and ICT
[Specialized Institution] National Research Foundation of Korea (NRF)
[Project Name] Bio, Medical Technology Development (R&D)
[Research Subject] Antibacterial/antithrombotic complex functional biomaterial and multifunctional cardio conduit surface modification technology development
[Contribution Rate] 1/4
[Research Managing Institution] AJOU UNIVERSITY INDUSTRY-ACADEMIC COOPERATION FOUNDATION
[Research Period] Apr. 1, 2018 through Jan. 31, 2019
[Supporting National Research and Development Project]
[Project Number] 2018M3A9E2023257
[Sponsor] Ministry of Science and ICT
[Specialized Institution] National Research Foundation of Korea (NRF)
[Project Name] Bio, Medical Technology Development (R&D)
[Research Subject] Development of Fundamental Technology for Biocompatible 3D Patch Materials
[Contribution Rate] 1/4
[Research Managing Institution] Korea Institute of Science and Technology
[Research Period] Apr. 1, 2018 through Dec. 31, 2018

FIELD OF THE INVENTION

The present invention is relevant to a preparation method of calcium peroxide-mediated in situ crosslinkable hydrogel as a sustained oxygen-generating matrix, and biomedical use thereof, more particularly, a new injection-type high-molecular hydrogel that can emit a high concentration of oxygen sustainably from a hydrogel matrix which can be produced based on the in situ crosslinkable hydrogel. Further, the in-situ crosslinkable hydrogel can be prepared by a new method for crosslinking hydrogel using calcium peroxide.

The present invention can be manufactured easier than existing method for preparing a hydrogel, and can regulate physical/chemical/biological properties of the hydrogel depending on the preparation conditions.

BACKGROUND OF THE INVENTION

Polymer hydrogels, which is made of a three-dimensional network of hydrophilic polymer, has been used widely in a variety of biomedical applications due to biocompatibility, high water content, excellent permeability of nutrients and metabolites, structural similarity to natural tissues and multi-tunable properties.

In particular, in situ crosslinkable hydrogel has been widely studied as a drug/cell carrier, a tissue filler or a support for tissue engineering based on minimally invasive techniques on the drug/cell carrier, tissue filler, or as a support for tissue engineering. The in situ crosslinkable hydrogel can be produced using natural and synthetic polymers, and can form a hydrogel through a variety of chemical and physical crosslinking.

Oxygen plays a key role in the in vivo homeostasis and wound treatment as a substrate and a signal molecule in the metabolism. To be more specific, a high concentration of oxygen increase oxygen partial pressure as well as active oxygen, and thereby make a cell secret growth factors that promote angiogenesis. Or a high concentration of oxygen induce a stem cell to migrate and thereby lead new blood vessel generation as well as wound healing. In this context, several recent technologies capable of carrying oxygen have been developed.

Examples are hyperbaric oxygen therapy (HBOT), hemoglobin-based oxygen carriers or perfluorocarbons-based oxygen carriers. The hyperbaric oxygen therapy (HBOT) is simple technology and is able to provide oxygen sustainably during treatment, and the oxygen carriers can release oxygen depending on oxygen partial pressure in the surrounding.

However, the former requires specialized facilities for treatment, and oxygen can be provided only by the breath in the former. The latter has a limitation that the initial release of oxygen occurs rapidly.

To solve this problem, a research of oxygen generating biomaterial under in situ for local oxygen delivery and sustainable oxygen delivery was progressed. Example of oxygen generating materials is typically hydrogen peroxide, sodium percarbonate and calcium peroxide.

However, the materials have shown limitations of a fast oxygen releasing pattern initially and the long-term oxygen release.

Therefore, it is necessary to develop in situ forming hydrogel with excellent biostability, which release high concentration oxygen sustainably excellent.

DETAILED DESCRIPTION OF THE INVENTION

Problems to be Solved

The present invention aims to solve the existing problems, and thus the technical goal of the present invention is to provide a new type of in situ crosslinkable polymer hydrogel releasing high concentration oxygen sustainably, a method for preparing a sustained oxygen-generating injection-type hydrogel, which controls physical/chemical/biological properties of the hydrogel, and a variety of biomedical applications thereof.

Solution

In order to solve the problem, the present invention manufactures an in situ crosslinkable polymer hydrogel using a natural/synthetic polymer having thiol group in an aqueous solution through inducing formation of disulfide bonds (—S—S) by decomposition of calcium peroxide, and provides a new type of in situ crosslinkable polymer hydrogel releasing a high concentration of oxygen sustainably by decomposition of calcium peroxide in an aqueous solution.

A natural/synthetic polymer having thiol group in the present invention is manufacture using Traut's reagent (TR), and thiol groups attached to backbone of a polymer can be adjusted according to an amount of TR used initially in synthesis.

Moreover, the present invention provides a method for preparing sustained oxygen-generating in situ crosslinkable hydrogel, which easily regulates physical/chemical/biological properties such as hydrogel formation time, mechanical strength, biodegradability and oxygen releasing behaviors, depending on adjustment of a polymer, calcium peroxide and TR affinity.

Further, the present invention provides a support for tissue regeneration or an implant material for filling.

The present invention provides a material for tissue adhesion or hemostasis.

The present invention provides a biologically active substance or a carrier for drug delivery.

Benefits of the Invention

A new type of in situ crosslinkable hydrogel according to the present invention is formed by oxygen generated by the decomposition of calcium peroxide, and can regulate a sustained-release behavior of the oxygen generated inside the hydrogel.

In other words, the present invention can overcome the limitations in the existing oxygen generation hydrogel, and make possible a variety of biomedical applications based on the excellent biocompatibility (e.g. tissue regeneration, artificial organisms manufacture, wound healing materials, tissue adhesive material, drug carrier etc.)

BRIEF DESCRIPTION OF THE DRAWINGS

FIG. 1 depicts a schematic diagram of GtnSH synthesis.

FIG. 2 depicts a schematic diagram of manufacturing a GtnSH hydrogel using calcium peroxide.

FIG. 3 depicts a graph of the thiol content in the gelatin derivative according to TR feed amounts.

FIG. 4 depicts a graph of the gelation time of hydrogels according to concentration of the polymer, concentration of calcium peroxide and concentration of TR feed amounts.

FIG. 5 depicts an oxygen release behavior of the hydrogel according to concentration of calcium peroxide and concentration of the polymer.

FIG. 6 depicts a graph of a mechanical strength of the hydrogel.

FIG. 7 depicts a graph of an enzymatic degradation degree of the hydrogel.

FIG. 8 depicts an image of biocompatibility of the hydrogel.

FIG. 9 depicts a graph of tissue adhesion of the hydrogel.

DETAILED DESCRIPTION OF THE INVENTION

Hereinafter, the present invention will be described in details.

The present inventors manufactured a new type of in situ hydrogel using calcium peroxide as a result of research, and have found that oxygen generated from the hydrogel was released sustainably for a long term (14 days or more). Additionally, the present inventor fabricated a polymer hydrogel material capable for releasing a high concentration of oxygen in a simple way, and have revealed that the physical/chemical/biological properties can be regulated easily.

The present invention induces disulfide bond by applying calcium peroxide to a natural/synthetic polymer having thiol group and thereby manufactures sustained oxygen-generating in situ hydrogel.

In FIG. 1, a backbone of the polymer having thiol group is manufactured using Traut's reagent (TR), and the thiol group in the backbone of the polymer can be adjusted depending on an amount of TR used initially in synthesis.

A backbone of the polymer can be one selected from a group consisting of gelatin, chitosan, heparin, cellulose, dextran, dextran sulfate, chondroitin sulfate, keratin, keratan sulfate, dermatan sulfate, alginate, collagen, albumin, fibronectin, laminin, elastin, vitronectin, hyaluronic acid, fibrinogen and multiple-arm polymer, but not limited thereto.

The multiple-arm polymer can be one or two or more polymers selected from a group consisting of one or more multiple-arm polyethylene glycols selected from a group consisting of 3-arm-polyethylene glycol (3armPEG), 4-arm-polyethylene glycol (4armPEG), 6-arm-polyethylene glycol (6armPEG) and 8-arm-polyethylene glycol (8armPEG); and tetronic series (4arm-PPO-PEO), but not limited thereto.

In FIG. 2, the sustained oxygen-generating hydrogel can be manufactured by inducing disulfide bond in the backbone having thiol group through oxidation under a solution comprising calcium peroxide.

The preparation method of oxygen-generating in situ crosslinkable hydrogel in the present invention can easily regulate physical-chemical properties such as gelation time, mechanical strength, and oxygen releasing behaviors, depending on an injection amount of thiol group, a concentration of a polymer and a concentration of calcium peroxide.

Moreover, the present invention can provide a support for tissue regeneration and tissue engineering or an implant material for filling comprising a sustained oxygen-generating in situ crosslinkable hydrogel.

The material can be one selected from a group consisting of cartilage regeneration, bone regeneration, alveolar regeneration, skin regeneration, cardiac tissue regeneration, artificial intraocular lens, spinal cord regeneration, cranial regeneration, vocal cord regeneration, vocal regeneration and augmentation, adhesion barrier, urinary incontinence treatment, wrinkles removal, wound dressing, tissue augmentation and intervertebral disc treatment, but not limited thereto.

Further, the present invention can provide a material for tissue adhesion or hemostasis comprising a sustained oxygen-generating in situ crosslinkable hydrogel.

The material for hemostasis can be applied to one selected from a group consisting of brain nerve surgery comprising vascular surgery, orthopedic surgery comprising bone adhesion, hemostasis for lacerated patients, suture of femoral arteries, suture of cataract incision, cartilage treatment, skin inosculation, hemostasis of organ/gland dissection surface, division-and-junction of a gastrointestinal tract and tendon/ligament treatment, but not limited thereto.

The present invention can provide a biologically active substance or a carrier for drug delivery comprising a sustained oxygen-generating in situ crosslinkable hydrogel.

The biologically active substance or drug can be one or two or more selected from a group consisting of a peptide or protein drug, an antimicrobial agent, an anti-cancer drug and an anti-inflammatory agent, but not limited thereto.

The peptide or protein drug can be one selected from a group consisting of fibroblast growth factor (FGF), vascular endothelial growth factor (VEGF), transforming growth factors (TGF), bone morphogenetic protein (BMP), human growth hormone (hGH), porcine growth hormone (pGH), granulocyte colony-stimulating factor (G-CSF), erythropoietin (EPO), macrophage colony-stimulating factor (M-CSF), tumor necrosis factor (TNF), epidermal growth factor (EGF), platelet-derived growth factor (PDGF), interferon-$\alpha$, $\beta$, $\gamma$, interleukin-2 (IL-2), calcitonin, nerve growth factor (NGF), growth hormone releasing factor, angiotensin, luteinizing hormone-releasing hormone (LHRH), luteinizing hormone-releasing hormone agonist (LHRH agonist), insulin, thyrotropin-releasing hormone (TRH), angiostatin, endostatin, somatostatin, glucagon, endorphins, bacitracin, colistin, bacitracin, monoclonal antibody, vaccine and a combination thereof, but not limited thereto.

The antimicrobial agent can be one selected from a group consisting of minocycline, tetracycline, ofloxacin, fosfomycin, profloxacin, ampicillin, penicillin, doxycycline, thienamycin, cephalosporins, norcadicin, gentamicin, neomycin, kanamycin, paromomycin, micronomicin, amikacin, tobramycin, dibekacin, cefotaxime, cephalosporin, erythromycin, ciprofloxacin, levofloxacin, enoxacin, vancomycin, imipenem, fusidic acid and a combination thereof, but not limited thereto.

The anti-cancer drug can be one selected from a group consisting of paclitaxel, taxotere, adriamycin, endostatin, angiostatin, mitomycin, bleomycin, cisplatin, carboplatin, doxorubicin, daunorubicin, idarubicin, 5-fluorouracil, methotrexate, actinomycin-D and a combination thereof, but not limited thereto.

The anti-inflammatory agent can be can be one selected from a group consisting of acetaminophen, aspirin, ibuprofen, diclofenac, indomethacin, piroxicam, fenoprofen, flurbiprofen, ketoprofen, naproxen, suprofen, loxoprofen, cinnoxicam, tenoxicam and a combination thereof, but not limited thereto.

Hereinafter, the present invention will be described in details based on examples. However, the examples are only for helping understand the present invention and the present invention is not limited thereto.

Example 1: Preparing Materials

Gelatin (type A from porcine skin, >300 bloom), 2-iminothiolane hydrochloride (TR), calcium peroxide ($CaO_2$), anhydrous Dimethyl Sulfoxide (anhydrous DMSO) and collagenase type II were purchased from Sigma Aldrich (St. Louis, Mo., USA).

Dulbecco's Modified Eagle's Medium; DMEM), penicillin-streptomycin (P/S), trypsin/EDTA and DPBS (Dulbecco's phosphate buffered saline; DPBS) solution were purchased form Gibco (Grand Island, N.Y., USA), Fetal Bovine Serum (FBS) was purchased from Research and Diagnostic Technology. Further, EGM-2 Single quots medium (Endothelial Cell Growth Medium; EGM) was supplied from Lonza. Moreover, Cell Proliferation reagent WST-1 was purchased from Roche Diagnostics, and Live/Dead Viability/Cytotoxicity Kit was purchased from Life science.

Other chemicals and solvents were used without additional purification.

Example 2: Structure and Synthesis of Gelatin Derivative Having Thiol Group (FIG. 1)

100 mg of gelatin was dissolved in 10 ml of anhydrous DMSO and the resulting solution was mixed with a solution where TR (1~20 mg) was dissolved in 1 ml of DMSO. The reaction temperature was 37° C. and the reaction was progressed under a nitrogen atmosphere for 24 hours.

The solution was sequentially dialyzed through a dialysis tube having 3,500 Da of molecular weight cutoff at 37° C., and media were replaced against a 5 mM HCl solution for a day followed by a 1 mM HCl solution for a day.

Thiolated gelatin (GtnSH) polymers were obtained through freeze-drying.

Example 3: Formation of a Hydrogel (FIG. 2)

Hydrogel was manufactured by mixing a solution in which GtnSH polymers were dissolved to DPBS at 37° C. with calcium peroxide (0-1% by weight).

Experiment 1: Adjusting an Amount of Thiol in GtnSH Depending on 2-iminothiolane Hydrochloride (TR) Feed Amounts (FIG. 3)

An amount of thiol in GtnSH was measured by Ellman's assay.

TR feed amount was 1 mg, 5 mg, 10 mg, 20 mg under constant composition of anhydrous DMSO (10 ml) and gelatin (100 mg) when synthesized for the purpose of analyzing the amount of thiol depending on TR feed amounts.

L-cystein as a standard and 100 μl of 1 mg/ml GtnSH solution were mixed with 100 μl of Ellman's reagent solution, and was placed at room temperature for 20 minutes.

Absorbance of the mixture was measured using Absorbance Detector at 405 nm, an amount of thiol in GtnSH was calculated using a standard curve of L-cystein.

As a result, an amount of thiol were controlled to 5.224~25.145 μmol/g (polymer) by adjusting the amount of TR feed, and as the amount of TR feed increased, the amount of thiol in GtnSH augmented.

When the amount of TR feed was increased from 10 mg to 20 mg, the amount of thiol in GtnSH was decreased because the amount of thiol in GtnSH was saturated.

Experiment 2: Gelation Time Depending on an Amount of Thiol (FIG. 4)

Gelation time depending on an amount of thiol was analyzed using vial tilting method.

TR feed amount was 1 mg, 5 mg, 10 mg, 20 mg under constant composition of GtnSH (5% by weight), $CaO_2$ (1% by weight) and DPBS (100 μl).

The result was that the gelation time of hydrogel was regulated at 3~42 minutes by adjusting the concentration of TR and as the amount of TR feed increased, the gelation time decreased. The reason can be explained as follows: the increased amount of TR feed augmented the amount of thiol in GtnSH and thereby functional groups capable of forming crosslink increased.

Experiment 3: Gelation Time Depending on a Concentration of Polymer (FIG. 4)

Gelation time depending on a concentration of polymer was analyzed using vial tilting method.

The concentration of GtnSH was 3% by weight, 5% by weight, 7% by weight under constant composition of TR feed (10 mg), $CaO_2$ (1% by weight) and DPBS (100 μl). More detailed conditions for manufacturing a hydrogel are described in Table 1.

TABLE 1

| Hydrogel | Composition |
| --- | --- |
| G3C1 | GtnSH 3 wt % + $CaO_2$ 1 wt % |
| G5C1 | GtnSH 5 wt % + $CaO_2$ 1 wt % |
| G7C1 | GtnSH 7 wt % + $CaO_2$ 1 wt % |

As a result, gelation time of the hydrogel was regulated at 2~6 minutes by adjusting the concentration of polymer. Further, as the concentration of polymer increased, the gelation time decreased. The reason can be explained as follows: functional groups attaching to the gelatin is increased due to the increased concentration of the polymer.

Experiment 4: Gelation Time Depending on a Concentration of Calcium Peroxide (FIG. 4)

Gelation time depending on a concentration of calcium peroxide was analyzed using vial tilting method.

The concentration of calcium peroxide was 0% by weight, 0.01% by weight, 0.05% by weight, 0.1% by weight, 0.5% by weight, 1% by weight under constant composition of TR feed (10 mg), GtnSH (5% by weight) and DPBS (100 μl). More detailed conditions for manufacturing a hydrogel are described in Table 2.

TABLE 2

| Hydrogel | Composition |
| --- | --- |
| G5C0 | GtnSH 5 wt % + $CaO_2$ 0 wt % |
| G5C0.01 | GtnSH 5 wt % + $CaO_2$ 0.01 wt % |
| G5C0.05 | GtnSH 5 wt % + $CaO_2$ 0.05 wt % |
| G5C0.1 | GtnSH 5 wt % + $CaO_2$ 0.1 wt % |
| G5C0.5 | GtnSH 5 wt % + $CaO_2$ 0.5 wt % |
| G5C1 | GtnSH 5 wt % + $CaO_2$ 1 wt % |

As a result, gelation time of the hydrogel was regulated at 5~329 minutes by adjusting the concentration of calcium peroxide. Further, gel was not formed in a solution where the concentration of calcium peroxide was under 0.01% by weight, but as the concentration of calcium peroxide increased, the gelation time of hydrogel decreased overall. The reason can be explained as follows: as the concentration of calcium peroxide increased, formation of hydrogen peroxide was promoted and thus disulfide bond formation by thiol groups was developed.

Experiment 5: Oxygen Release Behavior Depending on a Concentration of Calcium Peroxide (FIG. 5)

Oxygen release behavior depending on a concentration of calcium peroxide was analyzed using an oxygen sensor for 3 days.

The concentration of calcium peroxide was 0.5% by weight, 0.75% by weight, 1% by weight under constant composition of TR feed (10 mg) and GtnSH (5% by weight).

For measuring dissolved oxygen level in the media including the hydrogel, we manufactured a hydrogel (300 μl) and after 10 minutes, media (600 μl) were added to the hydrogel and dissolved oxygen level was measured.

As a result, the maximum dissolved oxygen level in the media was regulated at 46.22%~61.74% by adjusting the concentration of calcium peroxide. Further, as the concentration of calcium peroxide increased, the maximum dissolved oxygen level in the media increased. The reason can be explained as follows: as the concentration of calcium peroxide increased, oxygen generation was promoted and thus the amount of oxygen released from the hydrogel increased.

Experiment 6: Oxygen Release Behavior Depending on a Concentration of Polymer (FIG. 5)

Oxygen release behavior depending on a concentration of polymer was analyzed using an oxygen sensor for 3 days.

The concentration of polymer was 0% by weight, 3% by weight, 5% by weight, 7% by weight under constant composition of TR feed (10 mg) and $CaO_2$ (1% by weight).

For measuring dissolved oxygen level in the media including the hydrogel, we manufactured a hydrogel (300 μl) and after 10 minutes, media (600 μl) were added to the hydrogel and dissolved oxygen level was measured.

As a result, the maximum dissolved oxygen level in the media was regulated at 51.49%~86.12% by adjusting the concentration of polymer. Further, as the concentration of polymer increased, the maximum dissolved oxygen level in the media decreased but a high concentration of oxygen was maintained for a long time. The reason can be explained as follows: as the concentration of polymer increased, the level of crosslinking increased and thereby permeability of the hydrogel decreased, and consequently oxygen was released sustainably, not rapidly.

Experiment 7: Oxygen Release Behavior for a Long Term Depending on a Concentration of Calcium Peroxide (FIG. 5)

Oxygen release behavior depending on a concentration of calcium peroxide was analyzed using an oxygen sensor for 14 days.

The concentration of calcium peroxide was 0.5% by weight, 0.75% by weight, 1% by weight under constant composition of TR feed (10 mg) and GtnSH (5% by weight).

For measuring dissolved oxygen level in the media including the hydrogel, we manufactured a hydrogel (300 μl) and after 10 minutes, media (600 μl) were added to the hydrogel and dissolved oxygen level was measured.

As a result, the maximum dissolved oxygen level in the media was regulated at 23.68%~51.62% by adjusting the concentration of calcium peroxide. Further, as the concentration of calcium peroxide increased, the maximum dissolved oxygen level in the media increased. The reason can be explained as follows: as the concentration of calcium peroxide increased, oxygen generation was promoted and thus the amount of oxygen released from the hydrogel increased.

Moreover, we found that oxygens generated in the hydrogel were released for 14 days.

Experiment 8: Analysis of Elastic Modulus (FIG. 6)

Elastic modulus of GtnSH hydrogel depending on a concentration of calcium peroxide was analyzed using a rheometer.

The concentration of calcium peroxide was 0% by weight, 0.5% by weight, 0.75% by weight, 1% by weight under constant composition of TR feed (10 mg) and GtnSH (5% by weight).

We found that elastic modulus of GtnSH hydrogel can be regulated by adjusting a concentration of calcium peroxide, and the regulation scope was 100~810 Pa. Meanwhile, Gtn hydrogel was not formed in 0% by weight of calcium peroxide because disulfide bond between thiol groups did not formed due to absence of calcium peroxide.

Experiment 9: Analysis of Biodegradability of Hydrogel (FIG. 7)

For measuring biodegradability of hydrogel, we manufactured a hydrogel in a microtube by the same method as used in gelation time test.

The hydrogel was placed at room temperature for the purpose of stabilizing the hydrogel, and after 30 minutes, weight ($W_i$) of each of hydrogel was recorded. After that, the hydrogel was treated with DPBS or collagenase (0.01 mg/ml).

After removing supernatant every fixed time, the weight of hydrogel was measured and 200 μl of new media was added.

The biodegradability was calculated using [Equation. 1].

$$\text{Weight of hydrogels}(\%) = \frac{W_d}{W_i} \times 100 \qquad \text{[Equation 1]}$$

($W_d$ is weight of deteriorated hydrogel, and $W_i$ is weight of intact hydrogel)

As a result, hydrogels not treated with DPBS were not degraded but hydrogels treated with 0.01 mg/ml of collagenase were degraded over time. We found that hydrogels can be still degraded although thiol groups are attached to gelatin.

Experiment 10: Cyotoxicity of Hydrogel (FIG. 8)

For analyzing cell biocompatibility of GtnSH, cytotoxicity assay was performed by culturing human dermal fibroblasts (hDFBs) after GtnSH solution was placed in a 96-well plate.

The cell concentration in the assay was $2.0 \times 10^3$ cells/wells, and cell viability was measured using WST-1 assay after culturing the cells at 37° C., 5% $CO_2$ for 24 hours.

For analyzing cell biocompatibility of hydrogel, cytotoxicity assay was performed after forming a hydrogel including human umbilical vein endothelial cells (HUVEC) and culturing 3-dimensionally in a 96-well plate.

The cell concentration in the assay was $2.0 \times 10^5$ cells/wells, and cell viability was measured using Live/Dead Viability/Cytotoxicity Kit after culturing the cells at 37° C., 5% $CO_2$ for 7 days.

The hydrogel was manufactured mixing 0~50,000 U/ml of catalase for decomposition of hydrogen peroxide generated in a process of hydrogel formation.

In Live/Dead analysis, dead cells caused by cytotoxicity are red and live cells are green.

In the result, the GtnSH showed 90% or more of cell viability compared to control group, and 78-80% of live cells according to calcium peroxide were observed in the hydrogel as a result of Live/Dead assay. In other words, we found that cell biocompatibility of the hydrogel was excellent.

Experiment 11: Tissue Adhesive Strength of Hydrogel (FIG. 9)

Based on ASTM F2255-03 ("Test Method for Strength Properties of Tissue Adhesives in Lap-Shear by Tension Loading"), tissue adhesive strength of hydrogel in porcine skin was measured using universal testing machine (UTM).

Dimension of the porcine skin was 2.5 cm in diameter, and all areas of porcine skin were attached to a rectangular plastic plate using ethyl cyanoacrylate glue.

Before the test, surface of the porcine skin was washed for decellulariztion using 70% of isopropane with deionized water and 15 minutes after the washing, 100 μl of adhesives was applied to the porcine skin and then wrapped with two areas.

The adhered area was maintained at room temperature for 60 minutes under wet atmosphere after 100 G of pressure.

The sample was loaded in 10 mm/min of crosshead speed.

The maximum strength against displacement was measured and shear stress was used when destructed (the final adhesive strength) for identifying adhesive strength of each samples.

At least 5 samples were used for the test.

The result showed that the adhesive strength was improved as the concentration of calcium peroxide increased.

When the concentration of calcium peroxide was 0.5% by weight, 0.75% by weight, 1% by weight under constant composition of TR feed (10 mg) and GtnSH (5% by weight), the adhesive strength was regulated at 9.9~28.8 kPa, particularly the best adhesive strength in 1% by weight.

As described above, although described based on the detailed description and specific examples, the present invention is not limited thereto, and an ordinary skilled person in the art can make various modifications and variations within the equivalent scope of the following claims.

What is claimed is:

1. A preparation method of calcium peroxide-mediated in situ crosslinkable hydrogel as a sustained oxygen-generating matrix, comprising:
   a) reacting a natural or a synthetic polymer with Traut's reagent (TR) in a solvent, and synthesizing a polymer derivative having thiol group in backbone of the polymer derivative; and
   b) mixing and reacting a solution of the polymer derivative having thiol group with calcium peroxide ($CaO_2$), and thereby forming a hydrogel,
   wherein in the step b), disulfide bonds (—S—S) are induced between backbones of the polymer derivative having thiol group attached by decomposition of calcium peroxide ($CaO_2$), and thereby in situ crosslinking is formed.

2. The preparation method of the claim 1, wherein oxygen generated by the decomposition of calcium peroxide is released from the hydrogel sustainably.

3. The preparation method of the claim 1, wherein the natural or synthetic polymer in the step a) is one selected from a group consisting of gelatin, chitosan, heparin, cellulose, dextran, dextran sulfate, chondroitin sulfate, keratin, keratan sulfate, dermatan sulfate, alginate, collagen, albumin, fibronectin, laminin, elastin, vitronectin, hyaluronic acid, fibrinogen and multiple-arm polymer.

4. The preparation method of the claim 3, wherein the multiple-arm polymer is one or two or more polymers selected from a group consisting of one or more multiple-arm polyethylene glycols selected from a group consisting of 3-arm-polyethylene glycol (3armPEG), 4-arm-polyethylene glycol (4armPEG), 6-arm-polyethylene glycol (6armPEG) and 8-arm-polyethylene glycol (8armPEG); and tetronic series (4arm-PPO-PEO).

5. The preparation method of the claim 3, wherein the natural or the synthetic polymer in the step a) is gelatin.

6. The preparation method of the claim 1, wherein weight ratio of the natural or the synthetic polymer: Traut's reagent (TR) in the step a) is 100:1~20.

7. The preparation method of the claim 1, wherein the solvent in the step a) is anhydrous dimethyl sulfoxide (DMSO).

8. The preparation method of the claim 1, wherein the solution in the step b) is made by dissolving the polymer derivative having thiol group into Dulbecco's phosphate buffered saline (DPBS).

9. The preparation method of the claim 1, wherein the polymer derivative having thiol group in the step b) is used in amount of 3 to 7% by weight of reaction solution.

10. The preparation method of the claim 1, wherein the calcium peroxide in the step b) is used in amount of 0.01 to 1% by weight of reaction solution.

11. The preparation method of the claim 1, wherein under a condition of gelatin derivative (GtnSH) having thiol group 5% by weight and Traut's reagent (TR) 10 mg, and under condition of culture medium whose volume is twice volume of hydrogel, the formed hydrogel shows a high concentration of oxygen release behavior increasing the maximum amount of dissolved oxygen in the medium to 46.22%~61.74% as a concentration of calcium peroxide changes 0.5~1% by weight.

12. The preparation method of the claim 1, wherein under a condition of calcium peroxide 1% by weight and Traut's reagent (TR) 10 mg, and under condition of culture medium whose volume is twice volume of hydrogel, the formed hydrogel shows a high concentration of oxygen release behavior decreasing the maximum amount of dissolved oxygen in the medium to 86.12%~51.49% slowly as a concentration of gelatin derivative having thiol group changes 0~7% by weight.

13. The preparation method of the claim 1, wherein under a condition of gelatin derivative (GtnSH) having thiol group 5% by weight and Traut's reagent (TR) 10 mg, and under condition of culture medium whose volume is twice volume of hydrogel, the formed hydrogel shows a high concentration of oxygen release behavior increasing the maximum amount of dissolved oxygen in the medium to 23.68%~51.62% and releasing oxygen for 14 days or more as a concentration of calcium peroxide changes 0~1% by weight.

14. A sustained oxygen-generating in situ crosslinkable hydrogel synthesized according to claim 1.

15. The hydrogel of the claim 14, wherein the hydrogel is an injectable hydrogel.

16. A support for tissue regeneration and tissue engineering or an implant material for filling comprising a sustained oxygen-generating in situ crosslinkable hydrogel according to claim 14.

17. A material for tissue adhesion, wound healing or hemostasis comprising a sustained oxygen-generating in situ crosslinkable hydrogel according to claim 14.

18. A biologically active substance or a carrier for drug delivery comprising a sustained oxygen-generating in situ crosslinkable hydrogel according to claim 14.

* * * * *